United States Patent
Mercer

(10) Patent No.: US 7,757,562 B2
(45) Date of Patent: Jul. 20, 2010

(54) TECHNIQUE AND APPARATUS FOR DETECTING AND MONITORING INTERNAL DEFECT CONDITIONS OF MUD PUMPS

(75) Inventor: Jeffery Lyn Mercer, Mangham, LA (US)

(73) Assignee: MBH Data Source, Monroe, LA (US)

( * ) Notice: Subject to any disclaimer, the term of this patent is extended or adjusted under 35 U.S.C. 154(b) by 1543 days.

(21) Appl. No.: 10/281,776

(22) Filed: Oct. 28, 2002

(65) Prior Publication Data

US 2004/0079158 A1 Apr. 29, 2004

(51) Int. Cl.
G01N 29/00 (2006.01)
E21B 47/00 (2006.01)

(52) U.S. Cl. ............... 73/660; 73/152.04; 73/649; 73/861.23

(58) Field of Classification Search .......... 73/660, 73/659, 645, 861.23, 646, 649, 851.23, 644, 73/151, 152, 579, 599, 602, 152.04; 702/54, 702/56, 104; 367/81, 82, 83
See application file for complete search history.

(56) References Cited

U.S. PATENT DOCUMENTS

| | | | | | |
|---|---|---|---|---|---|
| 4,543,817 | A | * | 10/1985 | Sugiyama | 73/40.5 A |
| 4,726,231 | A | * | 2/1988 | Tretout et al. | 73/644 |
| 4,903,245 | A | * | 2/1990 | Close et al. | 340/853.3 |
| 5,115,672 | A | * | 5/1992 | McShane et al. | 73/596 |
| 5,223,207 | A | * | 6/1993 | Gross et al. | 376/216 |
| 5,257,545 | A | * | 11/1993 | Au-Yang | 73/597 |
| 5,329,465 | A | * | 7/1994 | Arcella et al. | 702/184 |
| 5,796,677 | A | * | 8/1998 | Kostek et al. | 367/25 |
| 5,852,587 | A | * | 12/1998 | Kostek et al. | 367/25 |
| 5,915,278 | A | * | 6/1999 | Mallick | 73/658 |
| 6,208,585 | B1 | * | 3/2001 | Stroud | 367/26 |
| 6,330,525 | B1 | * | 12/2001 | Hays et al. | 702/183 |
| 6,354,734 | B1 | * | 3/2002 | Curran et al. | 374/148 |
| 6,439,053 | B1 | * | 8/2002 | Bobulski | 73/579 |
| 6,601,005 | B1 | * | 7/2003 | Eryurek et al. | 702/104 |
| 6,637,267 | B2 | * | 10/2003 | Fiebelkorn et al. | 73/587 |
| 6,720,882 | B2 | * | 4/2004 | Davey | 340/611 |
| 6,829,542 | B1 | * | 12/2004 | Reynolds et al. | 702/34 |
| 6,976,503 | B2 | * | 12/2005 | Ens et al. | 137/552 |
| 2003/0192382 | A1 | * | 10/2003 | Mueller | |

OTHER PUBLICATIONS

Rockwell Software RSView32-index and chapter 5.

* cited by examiner

*Primary Examiner*—J M Saint Surin
(74) *Attorney, Agent, or Firm*—Harish Dhingra; Dhingra & Associates

(57) ABSTRACT

Technique for deterring and monitoring internal defect condition of a mud pump during the operation and/or in a laboratory conditions are illustrated. One or more acoustic transducers are attached in the proximity of one or more valves of the pump. Variation(s) in the output signal parameters are continuously monitored. Variation of the signal over the predetermined threshold level indicate a gradual degradation of the pump or if the variation of the signal occurs over a short interval it may indicate a sudden failure of the pump. Likewise, a system of detecting internal defect condition of the pump and apparatus for monitoring the pump condition is illustrated. The techniques are also applied to duplex and/or triplex high-pressure pumps used to push hydrocarbons through pipelines. Apparatus and system similar to that disclosed for the mud pump is equally applicable to the high-pressure pumps used to push hydrocarbons through pipelines.

31 Claims, 6 Drawing Sheets

FIG. 2
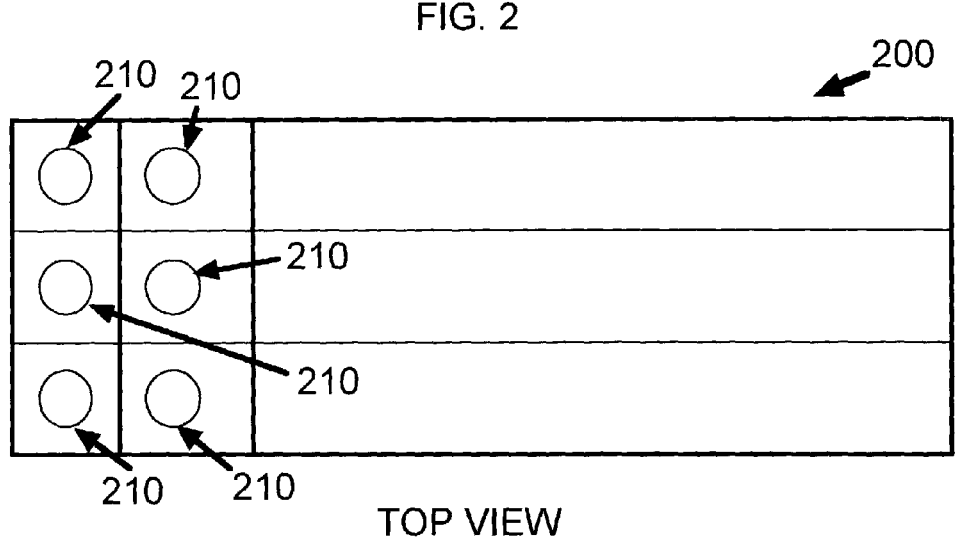
TOP VIEW
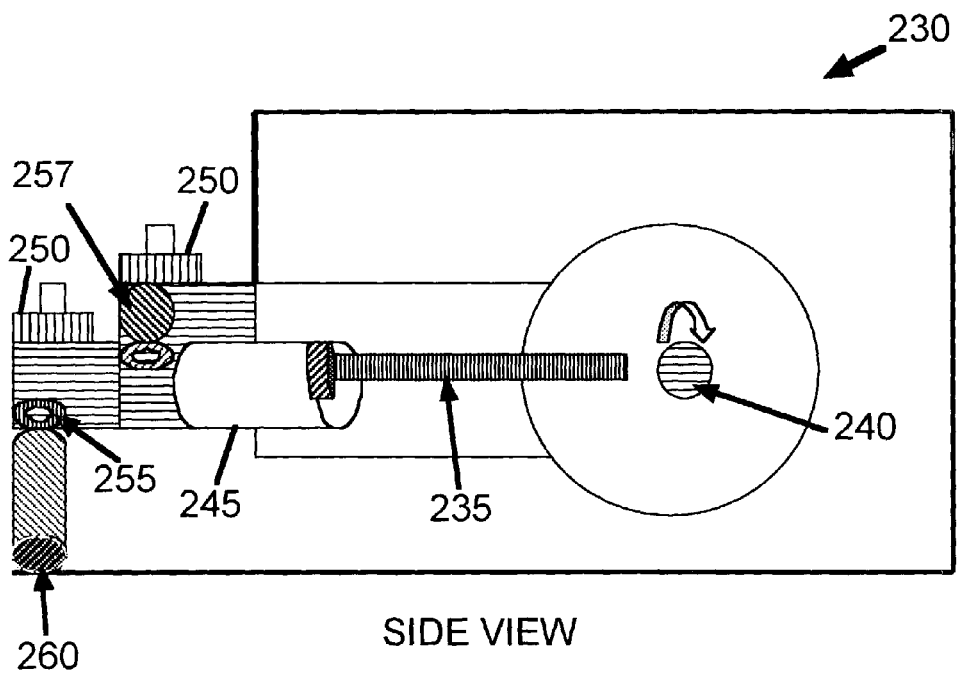
SIDE VIEW

FIG. 3
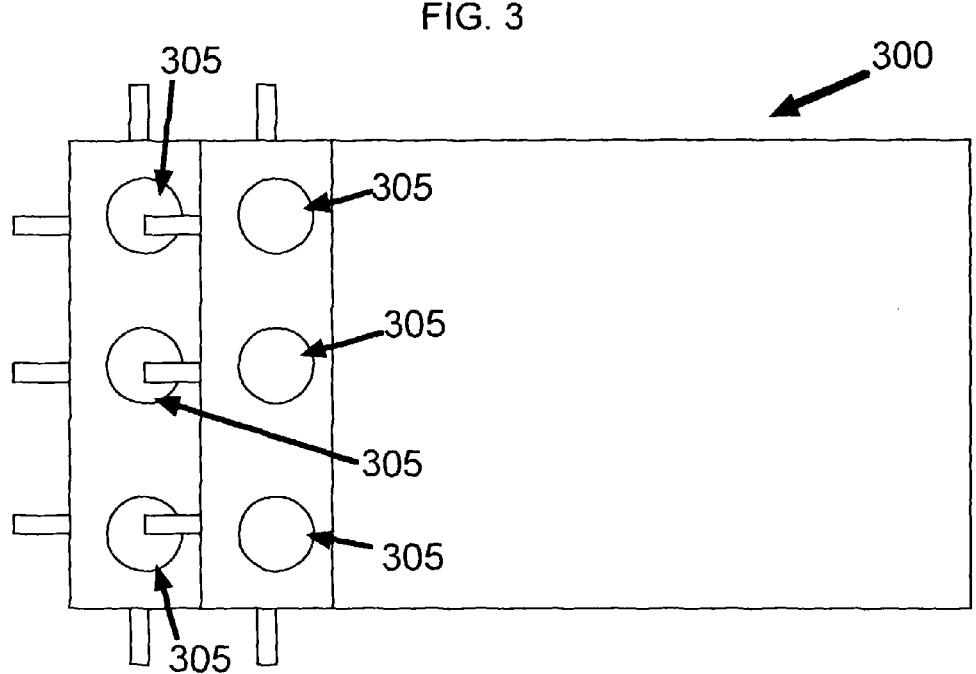
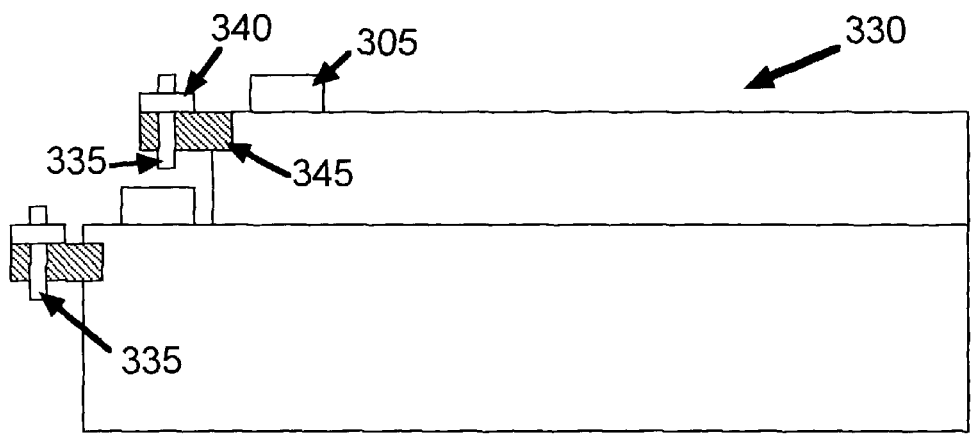

TECHNIQUE AND APPARATUS FOR DETECTING AND MONITORING INTERNAL DEFECT CONDITIONS OF MUD PUMPS

CROSS-REFERENCE TO RELATED APPLICATIONS

Not Applicable.

STATEMENTS REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Field of the Invention

This invention relates to mud pumps, and more specifically to detecting internal defect conditions of a mud pump and monitoring performance of the mud pump.

2. Description of the Related Art

In a drilling operation, whether offshore or on land, teeth of a drill bit grind the rock and break it into small pieces. These rock pieces must be continuously removed from the path of the drill bit for the operation to continue. To that end, a mud pump injects drilling fluid or mud fluid in the form of a jet to remove the cut rock pieces from the path of the drill bit so that the operation may continue. Thus, the mud pump plays the role of heart in keeping the mud fluid flowing to remove the broken rocks and facilitate movement of the drill bit. In modern drilling operations, without the operational mud pump(s), the drilling comes to a halt.

A mud pump is a large heavy-duty, high-pressure reciprocating pump. A typical pump is a single- or double acting, two or three-cylinder piston pump whose pistons travel in replaceable liners and are driven by a crankshaft actuated by an engine or a motor. The pump is typically positioned on the drilling platform.

The lubricating fluid also called mud is continuously used for drilling operations. The mud is usually placed in steel tanks on a rig, where the mud is circulated through the wellbore during drilling and well workover operations. In addition to its function of bringing cuttings to the surface, drilling mud cools and lubricates the bit and drill stem, protects against blowouts by holding back subsurface pressures, and deposits a mud cake on the wall of the borehole to prevent loss of drilling fluids to the formation.

The pump forces the drilling mud through the drill pipe and drill collars and to the drill bit. The drilling mud jets out from the bit nozzles with great speed and moves the debris out of the path of the drill bit. The contaminated mud then moves back up to the surface for filtering and further processing for reuse. Since the pump interior parts come in contact with the mud including rock pieces of varying sizes, and experience harsh environment including an extensive vibratory environment, damage may occur to those parts. In general, the pump components, like liners, valves, seats, etc., degrade gradually and it is difficult to determine when the pump may be suffer functional failure.

These mud pumps are expensive pieces of machinery and are integral to a drilling operation. When the mud pump breaks, drilling operations must stop, and either the drilling contractor or operator has to bear the expenses for the associated downtime. At current prices, these costs may run from $2,000 to $20,000 per hour. Down times of a few days can be very expensive. Many groups have experimented with mud pump monitors, but have tried to solve the problem by mounting detection and monitoring sensors inside the pump itself. These attempts have failed for two main reasons. Firstly, the sensors are exposed to a hostile environment like high pressures (up to 7500 PSI), excessive heat, and corrosive fluids where the sensors are easily damaged and become useless. Secondly, machine tolerances are so small in high-pressure pumps, like mud pumps, that attaching an additional piece (in the form of a replaceable sensor) is not only impractical but also adversely affects pump performance.

BRIEF SUMMARY OF THE INVENTION

Exemplary techniques for detecting internal defect conditions in a mud pump are illustrated. Acoustic signal(s) from the vicinity of at least one valve of the mud pump is sensed. The internal defect condition of the mud pump is determined according to pre-determined characteristics of the acoustic signal, which may be based on observation.

In other exemplary techniques for detecting and monitoring an internal defect condition in a mud pump is illustrated. Acoustic signal(s) from vicinity of at least one valve of the mud pump is sensed. The internal defect condition of the mud pump is determined according to pre-determined characteristics of the acoustic signal, which may be based on observation. The state of the pump valves is continuously monitored on display devices and/or recorded. When the defect condition occurs various communication means are utilized to inform the responsible personnel.

Apparatus for detecting and monitoring internal defect condition of a mud pump is illustrated. Acoustic transducer(s) are positioned in the proximity of valve(s) of the mud pump. Signal(s) from the acoustic transducer(s) are conditioned and processed to yield a number of relevant parameters. These relevant parameters are continuously monitored and/or recorded for post analysis. The condition of the pump is displayed on display devices and/or communicated to the responsible personnel.

BRIEF DESCRIPTION OF THE SEVERAL VIEWS OF THE DRAWINGS

A better understanding of the present invention can be obtained when the following detailed description of some embodiments is considered in conjunction with the following drawings in which:

FIG. 2 is an illustrative top view and a side view of the mud pump system of FIG. 1, indicating positioning of the sensor system according to the invention.

FIG. 3 is a top view and a side view of the mud pump system of FIG. 2, further illustrating positioning of the sensor(s) of the invention in proximity of the valve(s) of the mud pump.

DETAILED DESCRIPTION OF THE INVENTION

Figure 1:
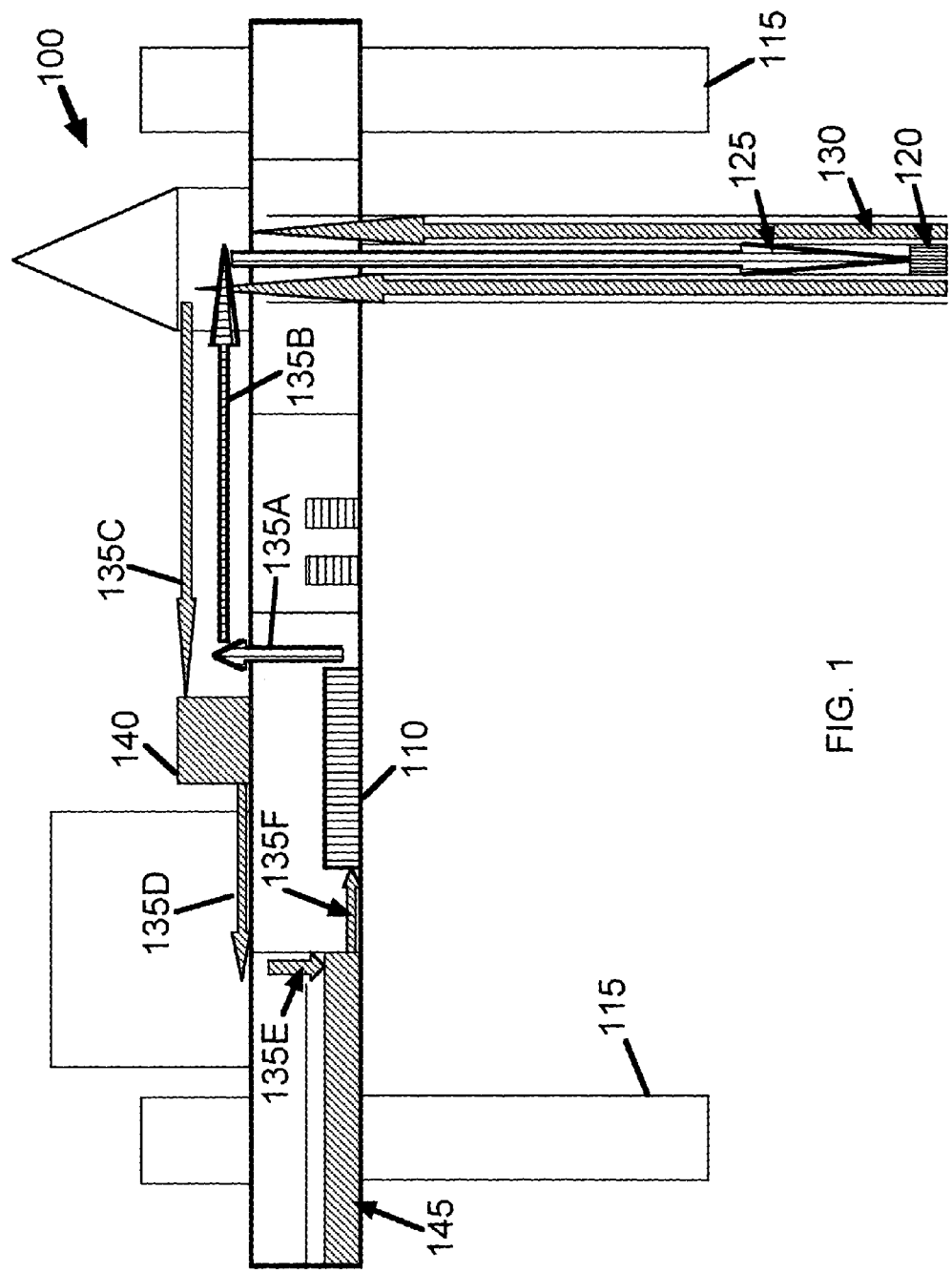
FIG. 1 is an illustrative side view of the drilling system in which the mud pump is used for pumping the mud and recycling the mud for continuous operation of the system

As noted above, there is a need for reliable diagnosis of mud pumps, and even more, there is a need for monitoring of mud pump operations where degradation of the pump's performance occurs gradually over a period of time. Referring to FIG. 1, is shown an illustrative side view of the drilling system 100 in which the mud pump 110 is used for pumping the mud and recycling the mud for continuous operation of the system. A typical offshore drilling platform is supported on a number of legs 115. The mud pump 110 pumps the mud through drill pipe 125 and jets on the rock cut by a drill bit 120 from where the mud mixed with rock pieces is carried to the surface through an annulus 130.

Still referring to FIG. 1, the path of the mud inflow through the drill pipe 125 from the mud pump 110 is shown by arrows 135a and 135b. The return path of the mud from the drill pipe 125 to a mud shaker house 140 is shown by the arrow 135c. The mud is filtered in the mud shaker house 140 where the rock debris is removed from the mud and it is sent to the mud pit 140 via the path of arrows labeled 135d and 135e. The mud pump 110 receives the mud from the mud pit 145 and pumps it again to the drill bit 120. Thus, the mud pumping and its recycling continues in the manner described.

Now referring to FIG. 2 is an illustrative top view 200 and a side view 230 of the mud pump system of FIG. 1, indicating positioning of the sensor system according to the invention. The top view illustrates a set of six valves of the mud pump 110. The mud pump may have a different number of valves. The side view 230 illustrates a shaft 240 driven by a motor or an engine (not shown) that causes a rod and piston 235 to reciprocate via eccentric gear in the pump piston linear cylinder 245. Each valve 210 has a valve cap 250. A centrifugal pump pumps mud from the mud tank 145 through a suction valve 255 into the mud pump 110. A discharge valve 257 is provided for discharge of the mud.

With reference to FIG. 3 is a top view 300 and a side view 330 of the mud pump system of FIG. 2, further illustrating positioning of the sensor(s) of the invention on the valve(s) of the mud pump 110. Each valve of the pump 110 may have a valve cap 305. A bracket 345 is attached to the valve and an acoustic sensor 335 is attached to the bracket 345 as explained below in more detail.

Figure 4:
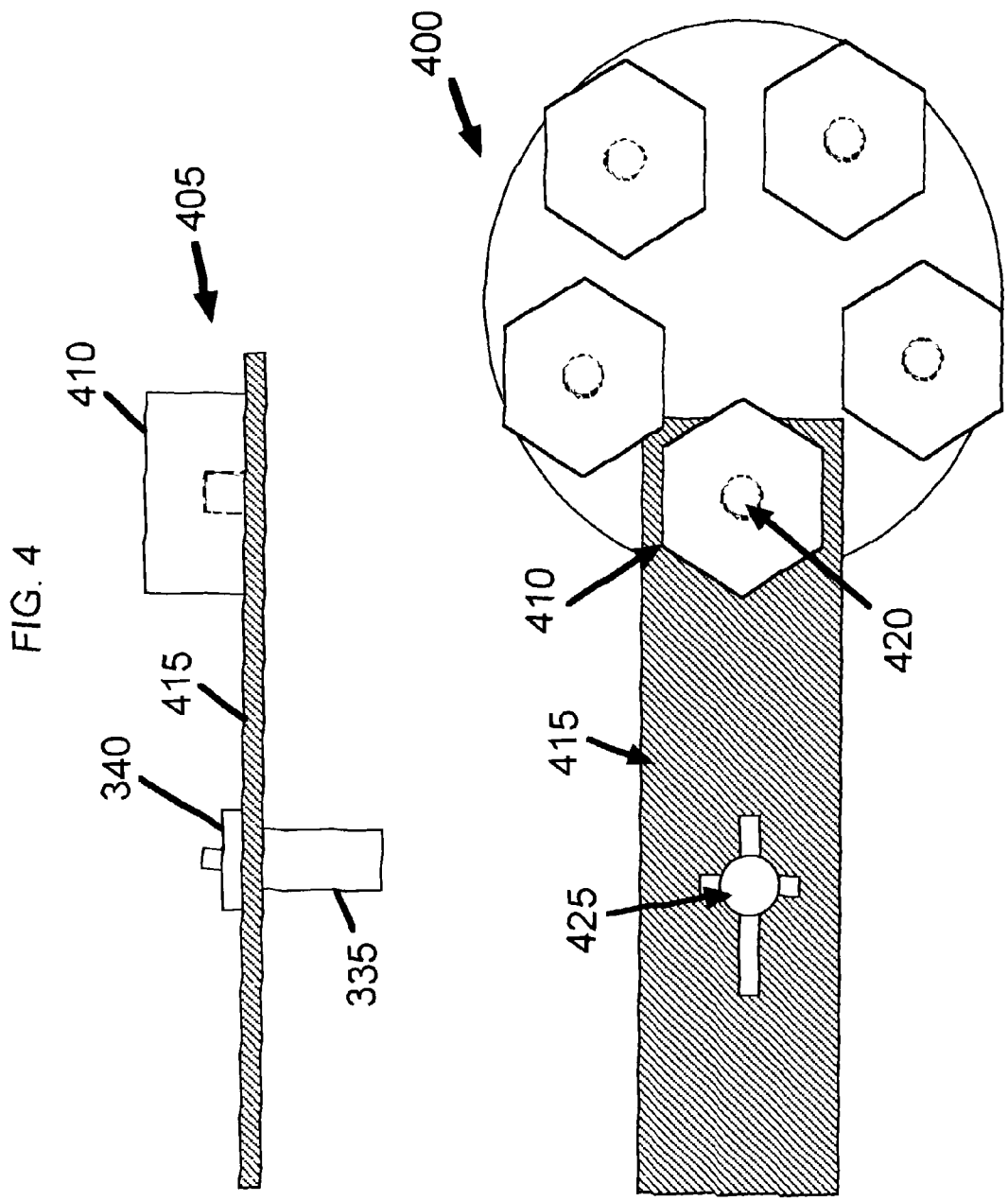
FIG. 4 is a top view and a side view of the mud pump system of FIG. 3, further illustrating details of the sensor attachment according to the invention.

Referring now to FIG. 4, are a top view 400 and a side view 405 of the mud pump system of FIG. 3, further illustrating details of the sensor attachment according to the invention. The side view 405 shows only one nut 410 of the valve while the top view 400 shows all six nuts of the exemplary embodiment. In the exemplary embodiment, a bracket 415 (roughly 6"×2") is positioned between the valve cap and the nut. The bracket 415 has a hole drilled in it that allows it to slide over the stud 420 that looks up at the nut. The nut 415 is tightened and the bracket 415 is secured. The sensor 335 is slid into a slot 425 cut at the opposite end of the bracket 415, and secured by a wing nut 340. This allows a quick and easy way to attach and remove the sensor 335, and encourages rig workers to remove the sensor while repairing pumps. The bracket 415 is non intrusive, and quick to install/remove. The bracket 415 transfers the acoustic signal from the valve cap 305 to the sensor 335.

Still referring to FIGS. 3 and 4, the bracket 415 may be permanently welded to the exterior of the pump as close as possible to the suction and discharge valves. The sensor 335 is attached to the bracket 415 with a wing nut as described above. Although the bracket 415 becomes permanently fixed, the sensor 335 is still easy to install/replace/or remove. Various modifications to the attachment may be made as would be apparent to those skilled in the art.

Figure 5:
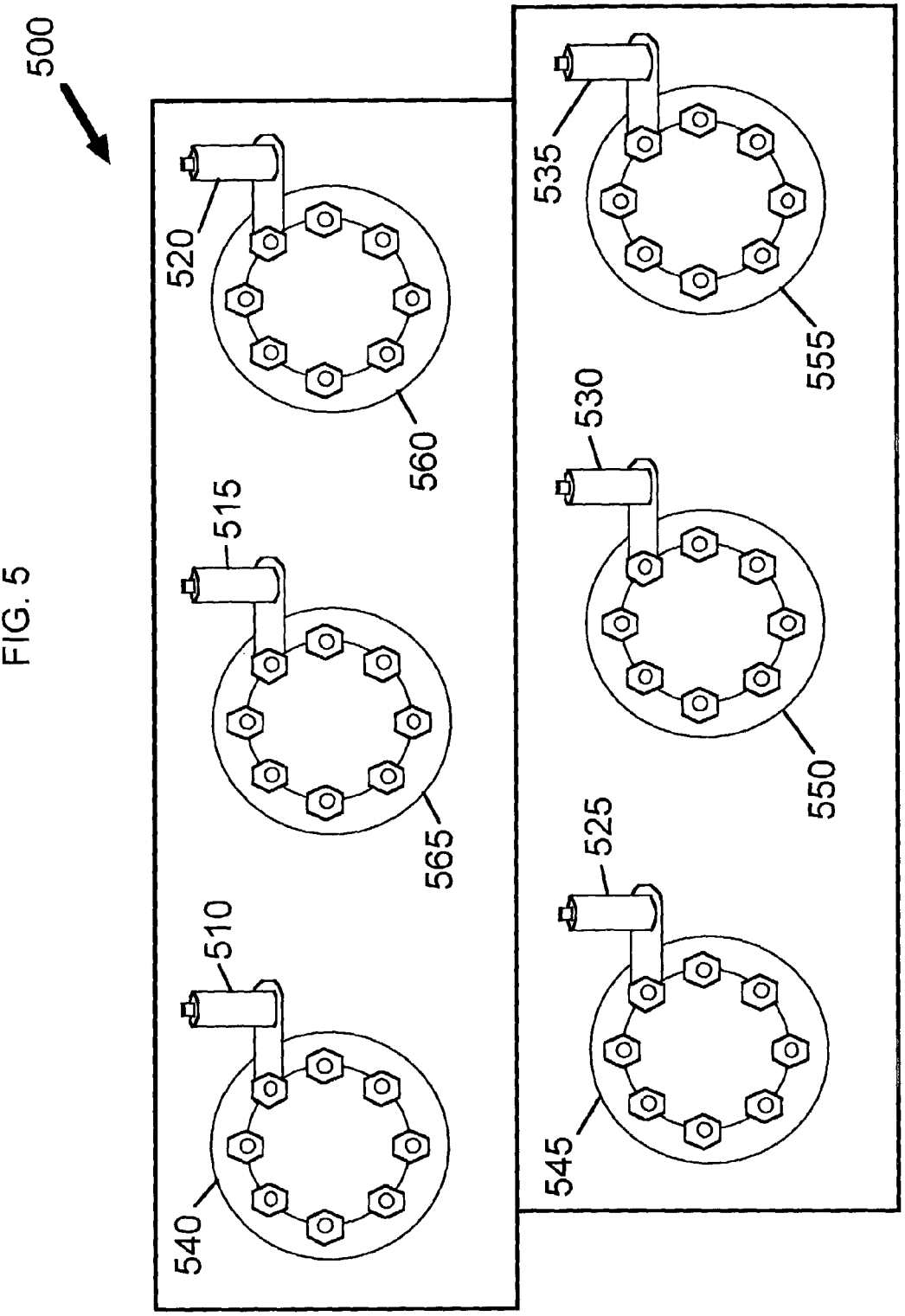
FIG. 5 is a top view of the sensor attachments on all the bolts of the mud pump according to one exemplary embodiment of the invention.

Referring to FIG. 5 is a top view 500 of the sensor attachments on all the bolts 540, 545, 550, 555, 560, and 565 of the mud pump according to one exemplary embodiment of the invention. Sensors 510, 515, 520, 525, 539, and 535 are attached to the bolts of each valve of the mud pump.

Figure 6:
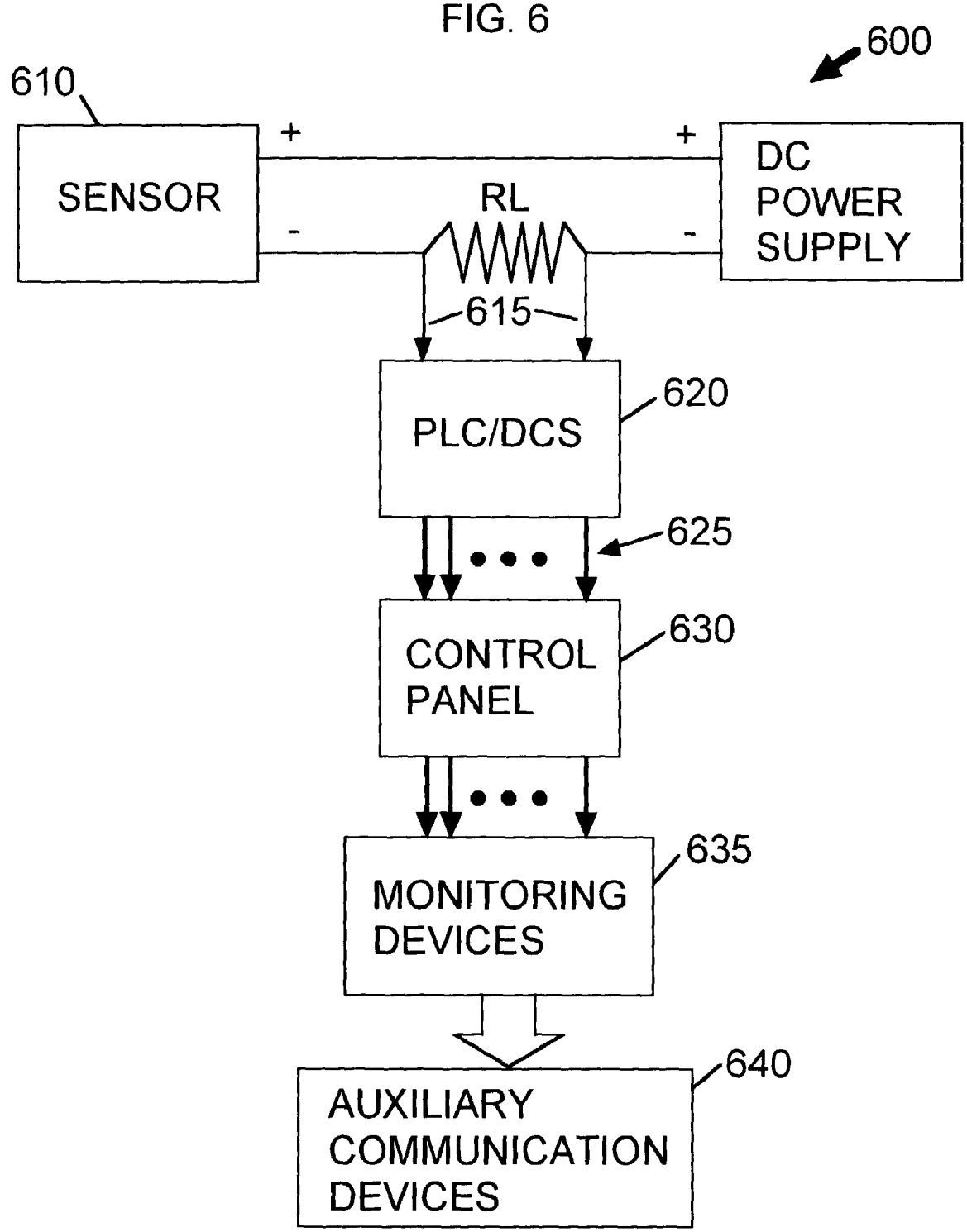
FIG. 6 is a schematic diagram of the sensor measurement and a monitoring control system according to another exemplary embodiment of the invention.

Referring to FIG. 6 is a schematic diagram of the sensor measurement and a monitoring control system and a technique 600 according to another exemplary embodiment of the invention. In block 610, an acoustic sensor 335, positioned in the proximity of at least one valve of the mud pump, senses an acoustic signal 615 from the vibration of the mud pump that is acquired across a load impedance $R_L$ or using any other technique. The signal 615 is then interpreted for determining the internal defect condition of the pump according to pre-determined characteristics as explained below in more detail. The signal 615, after processing, may be dynamically monitored on a real-time basis on monitoring devices 615, or may be recorded for later analysis in a laboratory or a similar place. The signal(s) may be recorded on magnetic media, optical media, and/or electronic memory media or combinations of media for delayed analysis/display and other purposes as would be apparent to those skilled in the art. Likewise, more than one acoustic sensors may be placed in the proximity of each valve and the detected signals may be combined together to improve signal to noise ratio, as would be apparent to those of skill in the art. In an exemplary embodiment, the acoustic sensor is a velocity loop powered sensor model number PC420V-20, manufactured by Wilcoxon Research of Gaithersburg, Md. This sensor is a 0=2.0 ips, peak sensor.

Still referring to FIG. 6, the signal 615 is sent to a Programmable Logic Controller PLC 620 where the signal 615 may be conditioned, e.g., filtered for unwanted noise, and/or amplified for further processing. The PLC 620 or any other commercially available auxiliary data storage memory device maintains a database of the time history of the signal level generated by each valve of the mud pump. Thus, the PLC may compute various parameters relating to the valve condition, for example, Alarm Set-points, Real-time Vibration values from each sensor, Pump "Strokes Per Minute", Alarm Tags, Data Log Values of each analog signal. At the same time, the PLC compares the current values of the parameters of interest with the stored historical values of the corresponding parameters. When the monitored parameter values of one or more parameter reach or exceed the pre-determined threshold values of the corresponding parameters, an indication of an internal defect condition is displayed and/or communicated to the maintenance personnel. The internal defect condition may be displayed on a monitoring device like a visual display or a paper tape and/or may be communicated by audio alarms, video displays/alarms, radio transmission, and/or e-mail to system maintenance personnel. In an example embodiment, a variation of five percent of the output signal amplitude over the historical trend from the acoustic transducer is set as threshold for determining the internal defect condition of the mud pump. Likewise, a different criterion of variation of other parameters of the output signal, for example, output power, a shift in properties of certain frequency components of the signal which may be substantially predictable in normal operation but change noticeably when an internal defect condition of the mud pump occurs, certain signal frequencies generated due to cavitation produced due to internal defect, and other variations of the criteria may be used to detect internal mud pump discrepancies leading to detection of internal defect conditions, as may be apparent to those skilled in the art.

Still referring to FIG. 6, the output signal 625 from the PLC 620 is transmitted to a control panel 630. An operator may select any number of aforementioned or other output signals from the PLC 620 for monitoring. The control panel 630 may also be used to select modes of aforementioned communications, for example during critical periods of operation, the operator may select audio alarms, while during non-critical periods of operation the operator may select only e-mail communication. Thus, the control panel 630 provides choices of displaying the signals of interest on the monitoring devices 635 and/or using auxiliary communication devices 640, including recording devices, for communicating the internal defect condition and data recording. An off the shelf computer program, called RSLogix 500, Copyright 1995-2001, from the Rockwell Corporation is used for programming the PLC. Making such choices of displaying different parameters using a PLC and other variations thereof is well within the skills of those practicing the art. Similarly an off the shelf program from the Rockwell Corporation, called RSView32 Works version 6.30.16, is used for computing the parameters for displaying on the monitoring devices 635. These software packages provide essentially capabilities to select the desired parameters and to display the same.

High-pressure pumps (similar to mud pumps) are used to push fluids (oil and gas) through pipelines. These pumps face the same potential problems as mud pumps (i.e. ripped seals, washed out valves etc.). When these high-pressure pumps shut down due to pump failure, gas no longer flows through the pipeline and revenue is lost. As a result, pipeline companies face the same costly pump 'downtime' issues as drilling contractors. A monitoring system, based on same principle and acoustic sensor techniques illustrated for the mud pump, warns operators of impending pump problems before the situation becomes critical and allows the operator to monitor these remote pumping stations, via satellite, from a central office or other means illustrated in the context of the mud pump methods, apparatus, and the system for monitoring.

The foregoing disclosure and description of the preferred embodiments are illustrative and explanatory thereof, and various changes in the components, the sensor configurations, configurations of the techniques, and configurations of the system, as well as in the details of the illustrated apparatus and techniques of operation may be made without departing from the spirit and scope of the invention as claimed in the appended claims.

What is claimed is:

1. A method of detecting an internal defect condition in a mud pump, the method comprising:
   a. sensing an acoustic signal from a location close to at least one valve of the mud pump to optimize signal to noise ratio; and
   b. determining the internal defect condition based on a pre-determined characteristics of the acoustic signal, wherein the pre-determined characteristics of the acoustic signal comprises a signal amplitude threshold.

2. The method as in claim 1, wherein the sensing comprises detecting a response of an acoustic sensor during the mud pump operation.

3. The method as in claim 1, wherein the sensing comprises detecting a response of an acoustic sensor during the mud pump testing.

4. The method as in claim 1, wherein the sensing further comprises recording on a media.

5. The method as in claim 4, wherein the recording is on a magnetic storage media.

6. The method as in claim 4, wherein the recording is on an optical storage media.

7. The method as in claim 4, wherein the recording is on an electronic memory media.

8. The method as in claim 1, wherein the acoustic signal comprises an accelerometer response from the at least one valve.

9. The method as in claim 1, wherein the acoustic signal comprises a velocity response from the at least one valve.

10. The method as in claim 1, wherein the acoustic signal comprises a frequency spectrum of the response from the at least one valve.

11. The method as in claim 1, wherein the internal defect condition comprises an internal mud pump discrepancy leading to a degraded performance.

12. The method as in claim 1, wherein the internal mud pump discrepancy comprises excessive wear of an internal part of the mud pump.

13. The method as in claim 1, wherein the internal mud pump discrepancy comprises break down of an internal part of the mud pump.

14. A method of detecting an internal defect condition in a mud pump, the method comprising:
   a. sensing an acoustic signal from a location close to at least one valve of the mud pump to optimize signal to noise ratio; and
   b. determining the internal defect condition based on a pre-determined characteristics of the acoustic signal, wherein the pre-determined characteristics of the acoustic signal comprises a phase variation threshold of certain frequencies of the acoustic signal.

15. A method of detecting an internal defect condition in a mud pump, the method comprising:
   a. sensing an acoustic signal from a location close to at least one valve of the mud pump to optimize signal to noise ratio; and
   b. determining the internal defect condition based on a pre-determined characteristics of the acoustic signal, wherein the pre-determined characteristics of the acoustic signal comprises a sensing of different frequency components.

16. A method of detecting an internal defect condition in a mud pump, the method comprising:
   a. sensing an acoustic signal from a location close to at least one valve of the mud pump to optimize signal to noise ratio; and
   b. determining the internal defect condition based on a pre-determined characteristics of the acoustic signal, wherein the pre-determined characteristics of the acoustic signal comprises detection of frequency components resulting due to cavitation in the mud fluid.

17. An apparatus for monitoring an internal defect condition in a mud pump, the apparatus comprising:
   a. an acoustic transducer adapted for coupling close to at least one valve of the mud pump to optimize signal to noise ratio;
   b. a signal conditioner coupled to the acoustic transducer; and
   c. a monitoring device coupled to the signal conditioner for communicating the valve condition, wherein the pre-determined characteristic of the acoustic signal comprises a signal amplitude threshold.

18. The apparatus as in claim 17, wherein the internal defect condition comprises an internal mud pump discrepancy leading to a degraded performance.

19. The apparatus as in claim 17, wherein the internal mud pump discrepancy comprises excessive wear of an internal part of the mud pump.

20. The apparatus as in claim 17, wherein the internal mud pump discrepancy comprises break down of an internal part of the mud pump.

21. The apparatus as in claim 17, wherein the internal mud pump discrepancy comprises failure of performance of an internal part of the mud pump.

22. The apparatus as in claim 17, wherein the acoustic transducer comprises an acceleration sensing transducer.

23. The apparatus as in claim 17, wherein the acoustic transducer further comprises an acceleration integrator to provide a velocity output.

24. The apparatus as in claim 17, wherein the signal conditioner comprises a signal amplifier.

25. The apparatus as in claim 17, wherein the signal conditioner further comprises a signal noise reduction circuitry.

26. The apparatus as in claim 17, wherein the signal conditioner further comprises a programmable logic controller (PLC).

27. The apparatus as in claim 17, wherein the PLC is programmed to output characteristics of the at least one valve.

28. The apparatus as in claim 17, wherein the output characteristics of the at least one valve comprises at least one of the signals corresponding to alarm set-points, real-time vibration values from each sensor, pump "strokes per minute", alarm tags, data log values of each analog signal.

29. An apparatus for monitoring an internal defect condition in a mud pump, the apparatus comprising:
   a. an acoustic transducer adapted for coupling close to at least one valve of the mud pump to optimize signal to noise ratio;
   b. a signal conditioner coupled to the acoustic transducer; and
   c. a monitoring device coupled to the signal conditioner for communicating the valve condition, wherein the predetermined characteristics of the acoustic signal comprises a sensing of different frequency components.

30. An apparatus for monitoring an internal defect condition in a mud pump, the apparatus comprising:
   a. an acoustic transducer adapted for coupling close to at least one valve of the mud pump to optimize signal to noise ratio;
   b. a signal conditioner coupled to the acoustic transducer; and
   c. a monitoring device coupled to the signal conditioner for communicating the valve condition, wherein the predetermined characteristic of the acoustic signal comprises detection of variation in the sensed acoustic signal power.

31. An apparatus for monitoring an internal defect condition in a mud pump, the apparatus comprising:
   a. an acoustic transducer adapted for coupling close to at least one valve of the mud pump to optimize signal to noise ratio;
   b. a signal conditioner coupled to the acoustic transducer; and
   c. a monitoring device coupled to the signal conditioner for communicating the valve condition, wherein the predetermined characteristics of the acoustic signal comprises detection of frequency components resulting due to cavitation in the mud fluid.

* * * * *